US012605181B2

(12) United States Patent
Barnes

(10) Patent No.: US 12,605,181 B2
(45) Date of Patent: Apr. 21, 2026

(54) TRIGGER THUMB TREATMENT DEVICES AND METHODS

(71) Applicant: SONEX HEALTH, INC., Eagan, MN (US)

(72) Inventor: Darryl E. Barnes, Eagan, MN (US)

(73) Assignee: SONEX HEALTH, INC., Eagan, MN (US)

( * ) Notice: Subject to any disclaimer, the term of this patent is extended or adjusted under 35 U.S.C. 154(b) by 510 days.

(21) Appl. No.: 18/102,990

(22) Filed: Jan. 30, 2023

(65) Prior Publication Data

US 2023/0240703 A1 Aug. 3, 2023

Related U.S. Application Data

(60) Provisional application No. 63/338,726, filed on May 5, 2022, provisional application No. 63/304,880, filed on Jan. 31, 2022.

(51) Int. Cl.
*A61B 17/3205* (2006.01)
*A61B 34/20* (2016.01)
*A61B 90/00* (2016.01)

(52) U.S. Cl.
CPC .......... *A61B 17/3205* (2013.01); *A61B 34/20* (2016.02); *A61B 2034/2063* (2016.02); *A61B 2090/034* (2016.02)

(58) Field of Classification Search
CPC ...... A61B 17/3211; A61B 2017/32113; A61B 17/3209; A61B 2017/320052;
(Continued)

(56) References Cited

U.S. PATENT DOCUMENTS

| | | | |
|---|---|---|---|
| 2,123,768 | A | 7/1938 | Corsico-Piccolini et al. |
| 3,435,826 | A | 4/1969 | Fogarty |

(Continued)

FOREIGN PATENT DOCUMENTS

| | | | |
|---|---|---|---|
| DE | 4444166 A1 | 6/1996 |
| EP | 3278749 A1 | 2/2018 |

(Continued)

OTHER PUBLICATIONS

Boretto, J., et al. "A prospective clinical study of the A1 pulley in trigger thumbs." Journal of Hand Surgery (European Volume) 33.3 (2008): 260-265. (Year: 2008).*

(Continued)

*Primary Examiner* — Thomas Mcevoy
(74) *Attorney, Agent, or Firm* — Seager, Tufte & Wickhem LLP

(57) ABSTRACT

A device for treating trigger thumb or trigger finger may include a handle, an introducer shaft extending from the handle, a blade shaft slidably disposed on the handle and the introducer shaft, a blade at or near a distal end of the blade shaft, a slider on the handle, attached to a proximal end of the blade shaft, for sliding the blade shaft and the blade distally and proximally along the introducer shaft, and a neurovascular guard slidably coupled with the handle and disposed over at least part of the blade shaft. The neurovascular guard may be made of a material that allows passage of ultrasound waves, such as Ultem, PEEK, PPS, or other polymers.

4 Claims, 14 Drawing Sheets

(58) Field of Classification Search
CPC .......... A61B 17/3205; A61B 17/32075; A61B
17/320036
See application file for complete search history.

(56) References Cited

U.S. PATENT DOCUMENTS

| 4,962,770 | A | 10/1990 | Agee et al. |
|---|---|---|---|
| 4,963,147 | A | 10/1990 | Agee et al. |
| 4,979,951 | A | 12/1990 | Simpson |
| 5,089,000 | A | 2/1992 | Agee et al. |
| 5,125,927 | A | 6/1992 | Belanger |
| 5,217,007 | A | 6/1993 | Ciaglia |
| 5,306,284 | A | 4/1994 | Agee et al. |
| 5,325,883 | A | 7/1994 | Orr |
| 5,345,927 | A | 9/1994 | Bonutti |
| 5,353,812 | A | 10/1994 | Chow |
| 5,425,355 | A | 6/1995 | Kulick |
| 5,480,408 | A | 1/1996 | Chow |
| 5,569,283 | A | 10/1996 | Green et al. |
| 5,620,446 | A | 4/1997 | McNamara et al. |
| 5,649,946 | A | 7/1997 | Bramlet |
| 5,655,545 | A | 8/1997 | Johnson et al. |
| 5,690,663 | A | 11/1997 | Stephens |
| 5,690,664 | A | 11/1997 | Sauer et al. |
| 5,702,417 | A | 12/1997 | Hermann |
| 5,707,382 | A | 1/1998 | Sierocuk et al. |
| 5,709,697 | A | 1/1998 | Ratcliff et al. |
| 5,735,865 | A | 4/1998 | Schaumann et al. |
| 5,755,732 | A | 5/1998 | Green et al. |
| 5,766,198 | A | 6/1998 | Li |
| 5,769,865 | A | 6/1998 | Kermode et al. |
| 5,769,895 | A | 6/1998 | Ripamonti |
| 5,772,680 | A | 6/1998 | Kieturakis et al. |
| 5,779,053 | A | 7/1998 | Partika et al. |
| 5,782,850 | A | 7/1998 | Ro |
| 5,782,854 | A | 7/1998 | Hermann |
| 5,800,449 | A | 9/1998 | Wales |
| 5,810,806 | A | 9/1998 | Ritchart et al. |
| 5,813,977 | A | 9/1998 | Hinchliffe et al. |
| 5,827,311 | A | 10/1998 | Berelsman et al. |
| 5,860,997 | A | 1/1999 | Bonutti |
| 5,865,728 | A | 2/1999 | Moll et al. |
| 5,893,861 | A | 4/1999 | Yumoto |
| 5,904,699 | A | 5/1999 | Schwemberger et al. |
| 5,908,433 | A | 6/1999 | Eager et al. |
| 5,954,739 | A | 9/1999 | Bonutti |
| 5,957,944 | A | 9/1999 | Khuri et al. |
| 5,968,061 | A | 10/1999 | Mirza |
| 6,004,337 | A | 12/1999 | Kieturakis et al. |
| 6,007,554 | A | 12/1999 | Van Ess |
| 6,012,586 | A | 1/2000 | Misra |
| 6,015,421 | A | 1/2000 | Echverry et al. |
| 6,017,356 | A | 1/2000 | Frederick et al. |
| 6,019,774 | A | 2/2000 | Weiss et al. |
| 6,030,402 | A | 2/2000 | Thompson et al. |
| 6,080,175 | A | 6/2000 | Hogendijk |
| 6,083,177 | A | 7/2000 | Kobren et al. |
| 6,106,496 | A | 8/2000 | Amnissolle |
| 6,113,617 | A | 9/2000 | van der Merwe |
| 6,117,153 | A | 9/2000 | Lary et al. |
| 6,168,608 | B1 | 1/2001 | Echeverry et al. |
| 6,171,236 | B1 | 1/2001 | Bonutti |
| 6,179,852 | B1 | 1/2001 | Strickland |
| 6,217,602 | B1 | 4/2001 | Redmon |
| 6,258,113 | B1 | 7/2001 | Adams et al. |
| 6,264,604 | B1 | 7/2001 | Kieturakis et al. |
| 6,346,085 | B1 | 2/2002 | Schiffman |
| 6,358,251 | B1 | 3/2002 | Mirza |
| 6,361,543 | B1 | 3/2002 | Chin et al. |
| 6,402,770 | B1 | 6/2002 | Jessen |
| 6,447,529 | B2 | 9/2002 | Fogarty et al. |
| 6,451,042 | B1 | 9/2002 | Bonutti |
| 6,514,272 | B1 | 2/2003 | Kieturakis et al. |
| 6,565,590 | B2 | 5/2003 | Kieturakis et al. |
| 6,592,602 | B1 | 7/2003 | Pearetree et al. |
| 6,632,234 | B2 | 10/2003 | Kieturakis et al. |
| 6,685,717 | B1 | 2/2004 | Ilic |
| 6,746,465 | B2 | 6/2004 | Diedrich et al. |
| 6,875,183 | B2 | 4/2005 | Cervi |
| 6,896,141 | B2 | 5/2005 | McMichael et al. |
| 7,001,405 | B2 | 2/2006 | Kieturakis et al. |
| 7,037,317 | B2 | 5/2006 | Hermann et al. |
| 7,214,236 | B2 | 5/2007 | Kieturakis et al. |
| 7,329,253 | B2 | 2/2008 | Brounstein et al. |
| 7,331,462 | B2 | 2/2008 | Steppe |
| 7,434,687 | B2 | 10/2008 | Itou et al. |
| 7,476,235 | B2 | 1/2009 | Diederich et al. |
| 7,481,817 | B2 | 1/2009 | Sauer |
| 7,504,875 | B2 | 3/2009 | Bhushan et al. |
| 7,520,886 | B2 | 4/2009 | Surti |
| 7,628,798 | B1 | 12/2009 | Welborn |
| 7,708,751 | B2 | 5/2010 | Hughes et al. |
| 7,744,617 | B2 | 6/2010 | Lunsford et al. |
| 7,780,690 | B2 | 8/2010 | Rehnke |
| 7,918,784 | B2 | 4/2011 | Wellborn et al. |
| 7,967,137 | B2 | 6/2011 | Fulbrook et al. |
| D645,147 | S | 9/2011 | Ruf |
| 8,052,710 | B2 | 11/2011 | Kambin et al. |
| 8,105,342 | B2 | 1/2012 | Onuki et al. |
| 8,147,487 | B2 | 4/2012 | Burbank et al. |
| 8,177,064 | B2 | 5/2012 | McCormick et al. |
| 8,246,646 | B2 | 8/2012 | Kambin |
| 8,252,013 | B2 | 8/2012 | Leibowitz et al. |
| D666,725 | S | 9/2012 | McCormack et al. |
| 8,257,379 | B2 | 9/2012 | Lee |
| 8,273,098 | B2 | 9/2012 | Strickland |
| 8,282,665 | B2 | 10/2012 | Kieturakis et al. |
| 8,323,278 | B2 | 12/2012 | Brecheen et al. |
| D673,683 | S | 1/2013 | McCormack et al. |
| D674,489 | S | 1/2013 | McCormack et al. |
| 8,348,966 | B2 | 1/2013 | McCormack et al. |
| 8,419,728 | B2 | 4/2013 | Klotz et al. |
| 8,449,478 | B2 | 5/2013 | Lee et al. |
| 8,500,770 | B2 | 8/2013 | Echevery et al. |
| 8,523,891 | B2 | 9/2013 | Welborn |
| 8,579,930 | B2 | 11/2013 | Palmer et al. |
| 8,603,124 | B1 | 12/2013 | Hatch |
| 8,603,738 | B2 | 12/2013 | Condeelis et al. |
| 8,608,738 | B2 | 12/2013 | Brecheen et al. |
| 8,608,763 | B1 | 12/2013 | Jurbala |
| 8,608,765 | B1 * | 12/2013 | Jurbala .......... A61B 17/320036 |
| | | | 606/170 |
| 8,613,745 | B2 | 12/2013 | Bleich |
| 8,652,157 | B2 | 2/2014 | McCormack et al. |
| 8,672,960 | B2 | 3/2014 | Briganti et al. |
| 8,702,654 | B2 | 4/2014 | Agee et al. |
| 8,721,668 | B2 | 5/2014 | McCormack et al. |
| 8,746,452 | B2 | 6/2014 | Tomes et al. |
| 8,753,364 | B2 | 6/2014 | McCormack et al. |
| 8,876,845 | B2 | 11/2014 | Suddaby |
| 8,906,040 | B2 | 12/2014 | Filipi et al. |
| 8,911,470 | B2 | 12/2014 | Mirza et al. |
| 8,951,273 | B1 | 2/2015 | Fard |
| 8,992,424 | B2 | 3/2015 | Orbay et al. |
| 9,017,354 | B2 | 4/2015 | Fink et al. |
| 9,028,516 | B2 | 5/2015 | Palmer et al. |
| 9,050,004 | B2 | 6/2015 | Diao et al. |
| D735,330 | S | 7/2015 | Rydberg et al. |
| D735,332 | S | 7/2015 | Allen et al. |
| 9,113,953 | B2 | 8/2015 | Smith |
| 9,131,951 | B2 | 9/2015 | Mirza et al. |
| 9,168,057 | B2 | 10/2015 | Poulsen |
| 9,186,217 | B2 | 11/2015 | Goyal |
| D745,675 | S | 12/2015 | Jankowski et al. |
| 9,532,847 | B2 | 1/2017 | Hendrickson et al. |
| 10,206,703 | B2 | 2/2019 | Palmer et al. |
| 10,245,062 | B2 | 4/2019 | Seymour |
| 10,383,609 | B2 | 8/2019 | Nakanishi et al. |
| 10,413,313 | B2 | 9/2019 | Brown et al. |
| D864,388 | S | 10/2019 | Barber |
| 10,575,867 | B2 | 3/2020 | Mirza et al. |
| 10,918,410 | B2 | 2/2021 | Mirza et al. |
| 11,006,970 | B2 | 5/2021 | Mirza et al. |
| 11,096,710 | B2 | 8/2021 | Mirza et al. |

(56) References Cited

U.S. PATENT DOCUMENTS

| | | | |
|---|---|---|---|
| 11,096,720 | B2 | 8/2021 | Mirza et al. |
| 11,259,837 | B2 | 3/2022 | Aklog et al. |
| D969,316 | S | 11/2022 | Milhous et al. |
| D974,561 | S | 1/2023 | Walsh |
| 2002/0120211 | A1 | 8/2002 | Wardle et al. |
| 2002/0161387 | A1 | 10/2002 | Blanco |
| 2002/0185406 | A1 | 12/2002 | Massengale et al. |
| 2004/0143280 | A1 | 7/2004 | Suddaby |
| 2004/0195131 | A1 | 10/2004 | Spolidoro |
| 2005/0209624 | A1 | 9/2005 | Vijay |
| 2005/0222598 | A1 | 10/2005 | Ho et al. |
| 2005/0228426 | A1 | 10/2005 | Campbell |
| 2006/0149136 | A1 | 7/2006 | Seto et al. |
| 2006/0190021 | A1 | 8/2006 | Hausman et al. |
| 2007/0083225 | A1 | 4/2007 | Kiser et al. |
| 2007/0112366 | A1 | 5/2007 | Welborn et al. |
| 2007/0118170 | A1 | 5/2007 | Kieturakis et al. |
| 2007/0225740 | A1 | 9/2007 | Suddaby |
| 2008/0033466 | A1 | 2/2008 | Assell et al. |
| 2008/0058588 | A1 | 3/2008 | Emanuel |
| 2008/0058846 | A1 | 3/2008 | Vosough |
| 2008/0109021 | A1 | 5/2008 | Medoff |
| 2008/0195128 | A1 | 8/2008 | Orbay et al. |
| 2008/0234713 | A1 | 9/2008 | Bernardini |
| 2008/0288041 | A1 | 11/2008 | Holman et al. |
| 2009/0048620 | A1 | 2/2009 | Weiss et al. |
| 2009/0048623 | A1 | 2/2009 | Lafosse et al. |
| 2009/0125044 | A1 | 5/2009 | Lary |
| 2009/0171157 | A1 | 7/2009 | Diederich et al. |
| 2009/0312740 | A1 | 12/2009 | Kim et al. |
| 2009/0312807 | A1 | 12/2009 | Boudreault et al. |
| 2010/0010530 | A1 | 1/2010 | Rhee |
| 2010/0100114 | A1 | 4/2010 | Berger |
| 2010/0125266 | A1 | 5/2010 | Deem et al. |
| 2010/0185222 | A1 | 7/2010 | Keller |
| 2010/0211082 | A1 | 8/2010 | Sauer |
| 2010/0249719 | A1 | 9/2010 | Fojtik |
| 2011/0087258 | A1 | 4/2011 | Sluss |
| 2011/0112563 | A1 | 5/2011 | To et al. |
| 2011/0118601 | A1 | 5/2011 | Barnes |
| 2011/0155599 | A1 | 6/2011 | Yakel et al. |
| 2011/0201881 | A1 | 8/2011 | Emch |
| 2012/0016398 | A1 | 1/2012 | Strickland |
| 2012/0029542 | A1 | 2/2012 | Huang |
| 2012/0029543 | A1 | 2/2012 | Lee |
| 2012/0191116 | A1 | 7/2012 | Flynn et al. |
| 2012/0198703 | A1 | 8/2012 | Ranieri et al. |
| 2012/0203220 | A1 | 8/2012 | Brannan et al. |
| 2012/0289987 | A1 | 11/2012 | Wilson et al. |
| 2012/0303018 | A1 | 11/2012 | Ladtkow et al. |
| 2013/0046323 | A1 | 2/2013 | Whitaker |
| 2013/0066149 | A1 | 3/2013 | Mirza et al. |
| 2013/0144318 | A1 | 6/2013 | Dinis Carmo |
| 2013/0165962 | A1 | 6/2013 | Porshinsky et al. |
| 2013/0172895 | A1 | 7/2013 | Wallace et al. |
| 2013/0197553 | A1 | 8/2013 | Ng et al. |
| 2013/0211201 | A1 | 8/2013 | Wongsiri |
| 2013/0289596 | A1 | 10/2013 | Guo |
| 2013/0345515 | A1 | 12/2013 | Fitzmaurice |
| 2014/0012076 | A1 | 1/2014 | Mirza et al. |
| 2014/0031621 | A1 | 1/2014 | Liu |
| 2014/0039533 | A1 | 2/2014 | Palmer et al. |
| 2014/0054356 | A1 | 2/2014 | Hartwick et al. |
| 2014/0066709 | A1 | 3/2014 | Mirza et al. |
| 2014/0180282 | A1 | 6/2014 | Brecheen et al. |
| 2014/0212456 | A1 | 7/2014 | Vazquez-Cintron et al. |
| 2014/0276741 | A1 | 9/2014 | McKay |
| 2014/0276790 | A1 | 9/2014 | Raybin et al. |
| 2014/0343357 | A1 | 11/2014 | Mirza et al. |
| 2014/0371526 | A1 | 12/2014 | Mirza et al. |
| 2015/0045822 | A1 | 2/2015 | Mirza et al. |
| 2015/0073461 | A1 | 3/2015 | McCormack et al. |
| 2015/0080878 | A1 | 3/2015 | Feng et al. |
| 2015/0080905 | A1 | 3/2015 | Begemann et al. |
| 2015/0133982 | A1 | 5/2015 | Park |
| 2015/0182248 | A1 | 7/2015 | Palmer et al. |
| 2015/0196743 | A1 | 7/2015 | Diederich et al. |
| 2015/0201959 | A1 | 7/2015 | Guo |
| 2015/0265818 | A1 | 9/2015 | Piskun et al. |
| 2015/0282832 | A1 | 10/2015 | Mirza et al. |
| 2015/0320436 | A1 | 11/2015 | Agee et al. |
| 2016/0081710 | A1 | 3/2016 | Barnes et al. |
| 2016/0157880 | A1 | 6/2016 | Aklog et al. |
| 2016/0235431 | A1 | 8/2016 | Brown et al. |
| 2017/0042565 | A1 | 2/2017 | Ellsworth et al. |
| 2017/0086803 | A1 | 3/2017 | Nakanishi et al. |
| 2017/0105792 | A1 | 4/2017 | Barnes et al. |
| 2017/0143364 | A1 | 5/2017 | Mirza et al. |
| 2019/0262024 | A1 | 8/2019 | Barnes et al. |
| 2019/0343546 | A1 | 11/2019 | Brown et al. |
| 2020/0078039 | A1 | 3/2020 | Mirza et al. |
| 2020/0107850 | A1 | 4/2020 | Mirza et al. |
| 2020/0197039 | A1 | 6/2020 | Hatch |
| 2021/0077139 | A1 | 3/2021 | Mirza et al. |
| 2021/0369293 | A1 | 12/2021 | Moungondo |
| 2022/0022909 | A1 | 1/2022 | Lins et al. |
| 2022/0346819 | A1 | 11/2022 | Barnes et al. |
| 2022/0354527 | A1 | 11/2022 | Barnes |

FOREIGN PATENT DOCUMENTS

| | | | |
|---|---|---|---|
| WO | 2007016141 | A2 | 2/2007 |
| WO | 2012089767 | A1 | 7/2012 |
| WO | 2013155472 | A1 | 10/2013 |
| WO | 2014118752 | A2 | 8/2014 |
| WO | 2014176206 | A2 | 10/2014 |
| WO | 2014176206 | A3 | 1/2015 |
| WO | 2020146458 | A1 | 7/2020 |
| WO | 2020243412 | A1 | 12/2020 |
| WO | 2020247476 | A1 | 12/2020 |

OTHER PUBLICATIONS

Invitation to Pay Additional Fees dated Mar. 31, 2023 for International Application No. PCT/US2023/011838.

U.S. Appl. No. 62/086,950, filed Dec. 3, 2014 (52 pages).

International Search Report and Written Opinion mailed Feb. 15, 2016, issued in International Application No. PCT/US2015/049558 (24 pages).

Examination Report issued in European Patent Application No. 15767038.1, dated Apr. 29, 2019 (8 pages).

International Search Report and Written Opinion mailed Mar. 25, 2022, in Application No. PCT/US22/70088.

International Search Report and Written Opinion issued Sep. 21, 2020, in International Application No. PCT/US20/35094.

Extended European Search Report for Application No. 20738258.1 dated Feb. 23, 2022.

International Search Report and Written Opinion mailed Jun. 15, 2020, in Application No. PCT/US20/12682.

International Search Report and Written Opinion dated Aug. 4, 2022 for International Application No. PCT/US2022/027039.

Muramatsu et al., "A Comparison of Blinded Versus Ultrasound-Guided Limited-Open Trigger Finger Release using the Yasunaga Knife," Journal of Hand Surgery, Asian Pacific, vol. 27, No. 1 pp. 124-129, Feb. 2022.

S2S Surgical™ Surgeon-2-Surgeon Innovation , Trigger Finger Release Surgial Technique, Version 1.1, 5 pages, www.S2Surgical.com 2017.

Extended European Search Report for EP Application No. 20814659.7 dated Jun. 15, 2023.

* cited by examiner

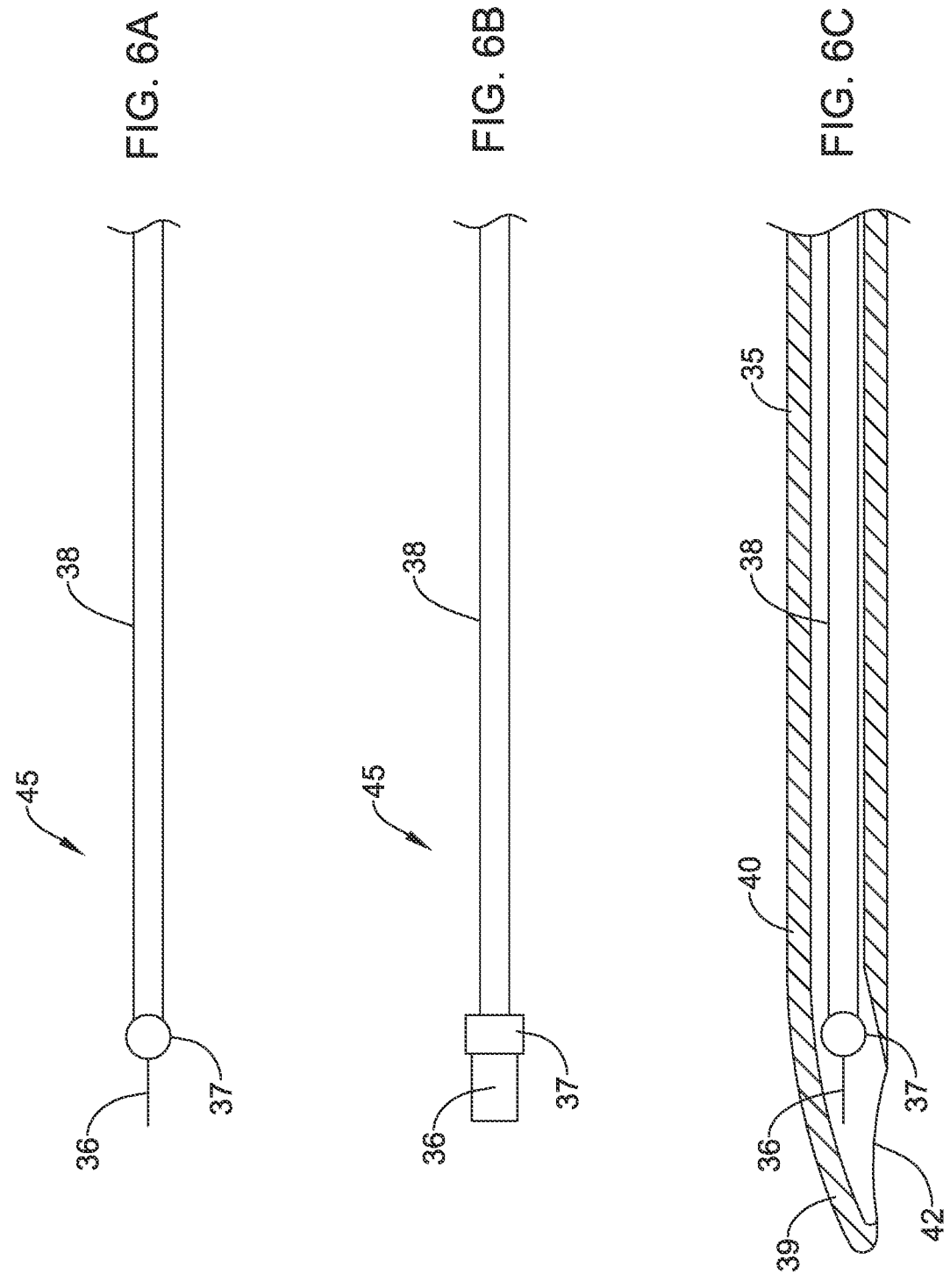

TRIGGER THUMB TREATMENT DEVICES AND METHODS

CROSS REFERENCE TO RELATED APPLICATIONS

This application claims priority to U.S. Provisional Application Nos. 63/304,880, filed Jan. 31, 2022, and 63/338,726, filed May 5, 2022, both of which are titled Trigger Thumb Treatment Device. The disclosures of the above-cited priority applications are hereby incorporated by reference in their entireties herein.

TECHNICAL FIELD

The present application relates generally to medical devices and methods. More specifically, the present application relates to devices and methods for treating trigger thumb.

BACKGROUND

As minimally invasive surgery has evolved, numerous tools have been developed to assist in treating medical conditions that have previously been treated with open and more invasive techniques. Treatment of trigger finger is one such example. The first annular ("A1") pulley is a small band of tissue on the palmar side of a person's hand. In some cases, the flexor tendon thickens, and a nodule can get caught on the A1 pulley and cause irritation and mechanical symptoms. The flexor tendon can then become locked in place when a person flexes his or her fingers. This condition is commonly referred to as "trigger finger." To treat trigger finger, the A1 pulley is typically cut, to release the tendon.

Trigger finger can occur in any of the five fingers. Due to the orientation of the thumb relative to the hand and due to the anatomy of the thumb, treating trigger thumb presents different challenges than treating the other four fingers. Specifically, the locations of nerves and muscles in the thumb, relative to the A1 pulley and the flexor pollicis longus tendon, make accessing and cutting the A1 pulley to treat trigger thumb technically difficult.

Therefore, it would be advantageous to have improved devices and techniques for treating trigger thumb. Ideally, such techniques would be minimally invasive or less invasive than traditional surgical approaches and would help prevent unwanted injury to surrounding neurovascular tissues. It would also be advantageous if such devices and methods could be used or adapted for use in other parts of the body, such as treating trigger finger in the other fingers or for treating impingement, entrapment, and compressive syndromes in areas other than the hand.

BRIEF SUMMARY

In one aspect of the present disclosure, a device for treating trigger thumb or trigger finger includes a handle, an introducer shaft extending from the handle, a blade shaft slidably disposed on the handle and the introducer shaft, a blade at or near a distal end of the blade shaft, a slider on the handle, attached to a proximal end of the blade shaft, for sliding the blade shaft and the blade distally and proximally along the introducer shaft, and a neurovascular guard slidably coupled with the handle and disposed over at least part of the blade shaft. In some embodiments, the neurovascular guard is made of a material that allows passage of ultrasound waves, such as but not limited to Ultem, PEEK, PPS, or other polymers. When the neurovascular guard is placed in an advanced position, a distal tip of the neurovascular guard may in some embodiments be located proximal of a distal tip of the introducer shaft, forming a gap through which the blade extends. The neurovascular guard may include a protrusion, which fits into a slot on the handle to allow the neurovascular guard to slide along the handle.

In another aspect of the present disclosure, a method for treating a thumb of a patient may involve: advancing an introducer shaft of a treatment device between an A1 pulley of the thumb and a flexor pollicis longus (FPL) tendon of the thumb; advancing a neurovascular guard shaft of the treatment device over the A1 pulley; exposing a blade out of a gap between a distal tip of the introducer shaft and a distal tip of the neurovascular guard shaft; retracting the blade to cut the A1 pulley; and removing the treatment device from the thumb. In some embodiments, the method may further involve visualizing at least part of the method using an ultrasound device positioned outside of the patient's hand. In some embodiments, the neurovascular guard shaft is made of a material that allows the passage of ultrasound signals therethrough.

The method may optionally further involve retracting the neurovascular guard shaft before removing the treatment device from the thumb. In some embodiments, retracting the blade to cut the A1 pulley involves sliding a slider on a handle of the treatment device. In some embodiments, exposing the blade comprises rotating the slider relative to the handle.

In another aspect of the present disclosure, a device for cutting a soft tissue in a body includes a handle, a shaft extending from the handle and comprising a distal opening, a blade housed within the shaft and configured to slide into and out of the distal opening in the shaft, and an anchoring tip attached to a distal end of the blade The device may also include a slider on the handle, attached to the blade, for advancing and retracting the blade out of and back into the distal opening of the shaft. In some embodiments, the blade includes at least two cutting edges.

The anchoring tip may be configured to anchor within another soft tissue, other than the soft tissue to be cut. In some cases, the anchoring tip has a sharp tip configured to pass through the soft tissue to be cut. For example, the soft tissue may be an A1 pulley in a thumb of a human hand. In some embodiments, the device may further include an introducer device through which the shaft, the blade, and the anchoring tip are introduced into a body. The introducer device may include a shaft portion made of a first material and a tip portion made of a second material. At least the second material may allow at least partial transmission of ultrasound signals, so that a portion of a device residing under or within the tip portion can be visualized using ultrasound.

In yet another aspect of the present disclosure, a method for treating a thumb of a patient may involve: advancing an anchoring tip of a treatment device through a thenar muscle and an A1 pulley of the thumb and into a flexor pollicis longus (FPL) tendon of the thumb; exposing a blade of the treatment device between a shaft of the treatment device and the anchoring tip; flexing the thumb, while maintaining the position of the anchoring tip in the FPL tendon, where upon flexion of the thumb, the blade of the treatment device cuts the A1 pulley; covering the blade with the shaft; and removing the treatment device from the thumb. In some embodiments, exposing the blade involves advancing the blade out of a distal opening in the shaft, using a slide on a handle of the treatment device. Alternatively, exposing the blade may involve retracting the shaft relative to the anchoring tip after the anchoring tip is anchored in the FPL tendon. In some embodiments, the method may also involve advancing an introducer device trough the thenar muscle, where the treatment device is advanced through the introducer device. In some embodiments, the method may further involve extending the thumb after flexing the thumb, to further cut the A1 pulley.

In another aspect of the present disclosure, a conduit device for facilitating delivery of a treatment device to a treatment site in a human or animal body may include a shaft portion and a tip portion. The tip portion includes a first material that allows at least partial transmission of ultrasound signals through the tip portion, so that a portion of the treatment device residing under or within the tip portion can be visualized using ultrasound. For example, the shaft portion and the tip portion may be made of the first material. Alternatively, the tip portion may be made of the first material, and the shaft portion may be made of a second material attached to the tip portion. The tip portion may include an acoustic window. Examples of the first material include but are not limited to ABS, polystyrene, nylon, polycarbonate, PETG copolyester, and glass-filled nylon.

BRIEF DESCRIPTION OF THE DRAWINGS

FIGS. 6A-6C are side, partial cross-sectional views of a trigger thumb treatment system, according to an alternative embodiment.

DETAILED DESCRIPTION

The soft tissue cutting devices and methods disclosed herein are primarily described for use in cutting an A1 pulley in a thumb to release/relieve tension on the flexor pollicis longus tendon and thus treat trigger thumb. In some embodiments, however, the trigger thumb treatment device may be used, or adapted for use, in other parts of the hand or body to cut other soft tissues. Therefore, although this application focuses on trigger thumb treatment, the devices and methods herein are not limited to that use. Furthermore, while the following descriptions are believed to be complete, the embodiments described are examples only. Any given embodiment may include features of other described embodiments or may be altered or adapted for alternative uses, without departing from the scope of the invention.

In this application, the term "distal" generally means "close to or in a direction toward target tissue," and the term "proximal" generally means "farther from or in a direction away from the target tissue." In other words, proximal and distal are relative terms. For example, when a user holds a treatment device and inserts one end of the treatment device into a patient to perform a treatment, the end of the device that is inserted into the patient will be referred to as the "distal end" of the device. The end of the device being held by the physician will be referred to as the "proximal end" of the device. Although these terms will be used consistently in this application, they should not be interpreted as limiting.

Figure 1:
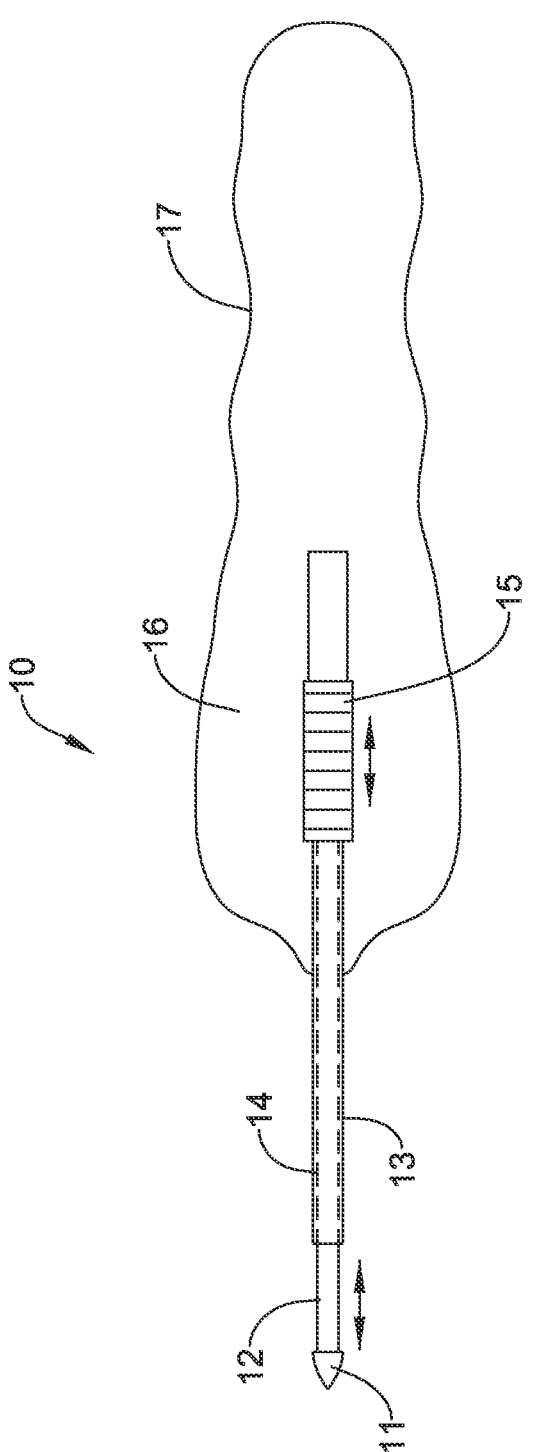
FIG. 1 is a top view of a trigger thumb treatment device, according to one embodiment.

Referring now to FIG. 1, one embodiment of a trigger thumb treatment device 10 (or simply "treatment device 10") is illustrated in top view. The treatment device 10 includes an anchoring tip 11 (or "tip anchor") attached to a blade 12, which extends to a blade shaft 14 (shown in broken lines as being covered). The treatment device 10 also includes a shaft 13 (or "outer shaft"), which is shown in FIG. 1 in cross section, so that the blade shaft 14 is visible within it. The shaft 13 is attached at its proximal end to a handle 16, which includes finger grip contours 17 (or "finger grips"). A slide 15 is attached to the handle 16 and the blade shaft 14. The slide 15 can serve one or more of several purposes. First, the slide 15 can include a push-down or other locking/unlocking mechanism that releases the anchoring tip 11 to allow it to extend away from the shaft 13 and thus expose the blade 12. In alternative embodiments, this tip release function may be achieved by a different mechanism, such as a button. Second, the slide 15 may be used for advancing and/or retracting the blade 12 out of and back into the shaft 13. In some embodiments, the anchoring tip 11 may be anchored in soft tissue released, and then the shaft 13 may be pulled proximally to expose the blade 12. The slide 15 may then be used, after the blade 12 has cut the target tissue, to pull the blade 12 back into the shaft 13 and the anchoring tip 11 back into contact with the shaft 13. In other embodiments, the slide 15 may also be used to advance the anchoring tip 11 at any point during the procedure.

The anchoring tip 11 has a sharp, pointed distal end, which facilitates passing it through soft tissue on the way to its targeted anchoring location. The blade 12 is flat and may have one or multiple cutting edges. As explained further below, the anchoring tip 11 is anchored in soft tissue just beyond another soft tissue that is to be cut. After the anchoring tip 11 is anchored, the blade 12 is exposed, typically by retracting the shaft 13 proximally while the anchoring tip 11 remains in the same location. The soft tissue in which the anchoring tip 11 is anchored is then moved in approximately a lateral direction, relative to the shaft 13, for example by having the patient flex and extend his/her thumb. This movement causes the anchoring tip 11 to move the blade 12 through the soft tissue that is targeted for cutting, thereby cutting the tissue. Further details of this method and the treatment device 10 are provided below.

Figures 2A, 2B:
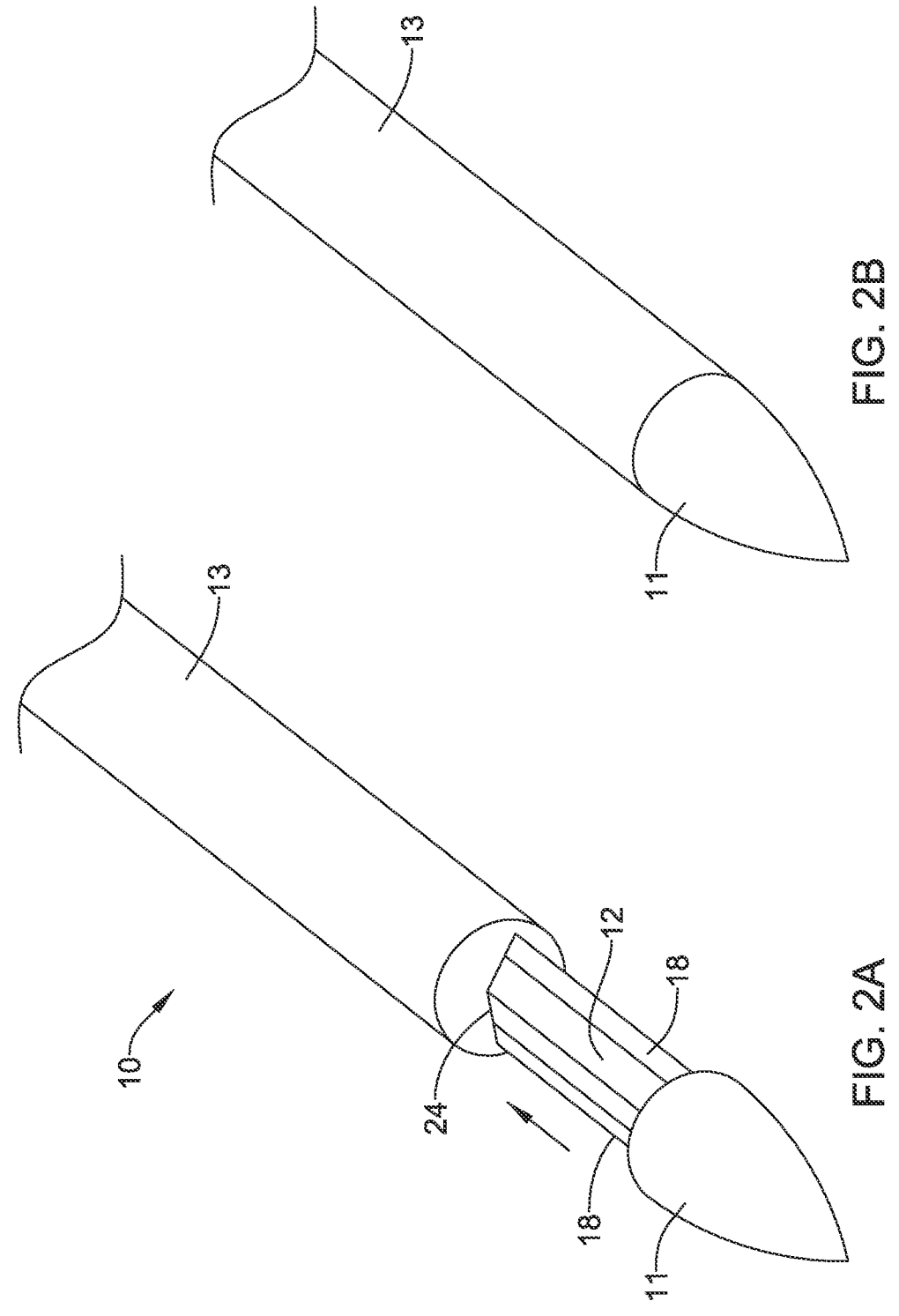
FIGS. 2A and 2B are perspective views of a distal portion of the trigger thumb treatment device of FIG. 1, shown in a blade active configuration (FIG. 2A) and a blade inactive configuration (FIG. 2B), according to one embodiment.

FIGS. 2A and 2B are perspective views of a distal portion of the trigger thumb treatment device 10, including a distal portion of the shaft 13, the blade 12, and the anchoring tip 11. The blade 12 may include multiple cutting edges 18, as shown. FIG. 2A illustrates the treatment device 10 in an active (or "blade active") configuration or position. In the active position, the anchoring tip 11 is extended distally away from the distal end of the shaft 13, and the blade 12 has been advanced out of an opening 24 in the distal end of the shaft 13 to expose the blade 12. It is in this active position that the blade 12 is used to cut the targeted soft tissue, such as the A1 pulley in the thumb.

FIG. 2B illustrates the treatment device 10 in an inactive (or "blade inactive") configuration or position. Generally, the treatment device 10 is advanced into the patient and removed from the patient in the inactive position. In some cases, however, it may be acceptable to remove the device 10 from the patient in the active position. As evident from FIGS. 2A and 2B, the anchoring tip 11 may have a bullet shape with a sharp distal tip, which facilitates advancing the anchoring tip 11 through soft tissue with minimal or no tissue damage. Once the anchoring tip 11 is positioned in a desired location, the wider, proximal end of the anchoring tip 11 helps to hold it within the tissue.

Figure 3:
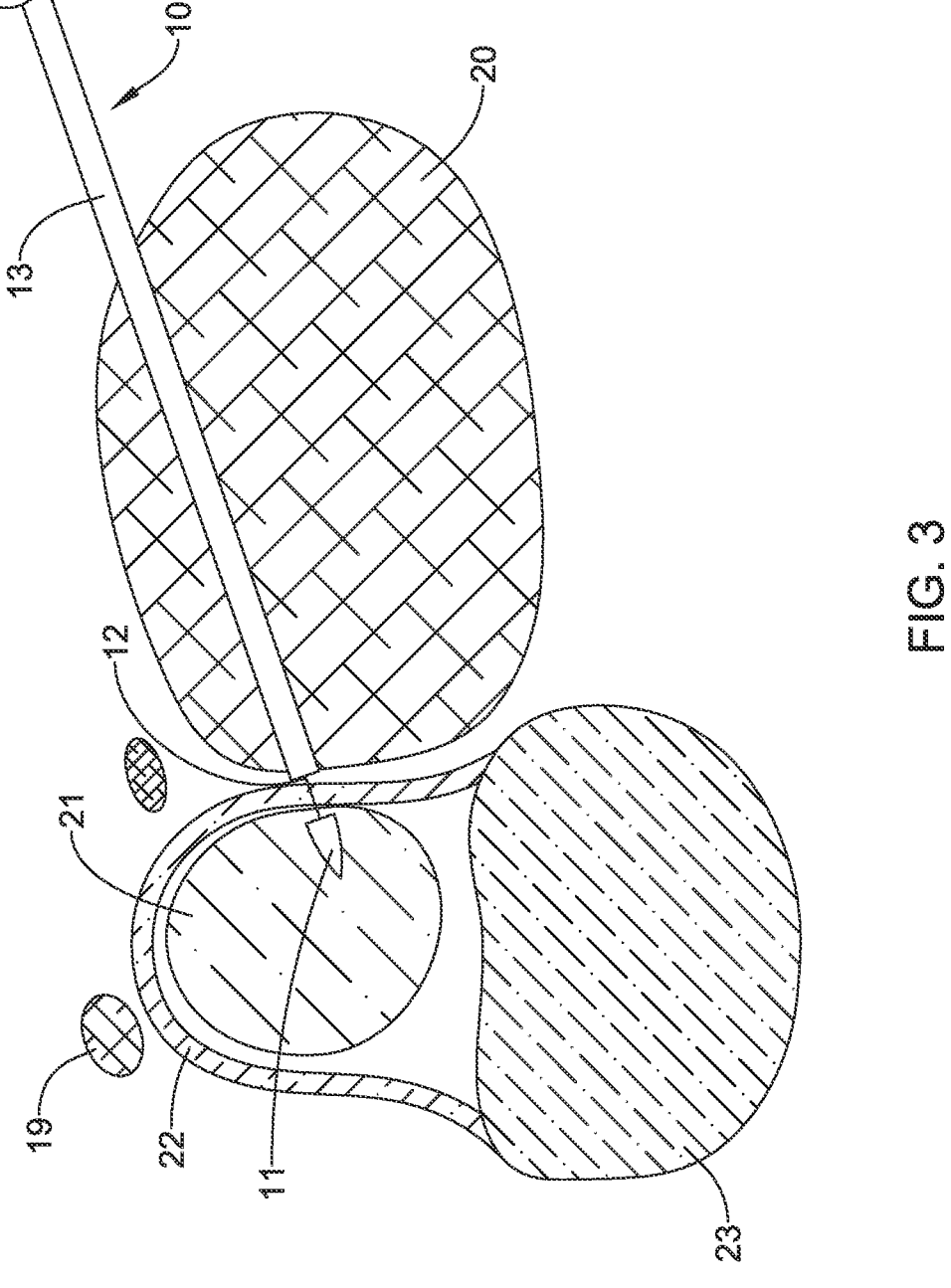
FIG. 3 is a partial cross-sectional view of a portion of a thumb, illustrating a method of using the trigger thumb treatment device of FIGS. 1-2B to cut the A1 pulley of the thumb, according to one embodiment.

FIG. 3 illustrates placement of the trigger thumb treatment device 10 in a thumb, where the anatomy around the thumb is shown in cross section and the trigger thumb treatment device 10 is shown from a side view. The illustrated portions of the thumb are the proper digital nerve 19, the thenar muscle 20, the flexor pollicis longus (FPL) tendon 21, the A1 pulley 22, and the first metacarpal bone 23. In use, the trigger thumb treatment device 10 may be advanced in a slightly oblique direction, in its inactive configuration and using ultrasound guidance, through the patient's skin, subcutaneous tissue, thenar muscle 20, and A1 pulley 22 near its radial origin. When the anchoring tip 11 has passed into the FPL tendon 21, the treatment device 10 is in the desired position. At this point, the slide 15 on the handle 16 of the treatment device 10 is used to release the anchoring tip 11 from the shaft 13, thus allowing the anchoring tip 11 to act as an anchor in the FPL tendon 21. In other embodiments, the slide 15 may be replaced by a button or other mechanism for releasing the anchoring tip 11. Once the anchoring tip 11 is released, the shaft 13 is pulled back proximally to expose the cutting blade 12 between the anchoring tip 11 and the distal end of the shaft 13. Ultrasound may be used to verify separation of the shaft 13 from the anchoring tip 11. The thumb is then flexed, for example by asking the patient to flex his/her thumb at the interphalangeal joint. Alternatively, the physician may manually flex the patient's thumb. In either case, flexion of the thumb causes the anchoring tip 11 to be pulled proximally within the A1 pulley 22, thus pulling the cutting blade 12 through the A1 pulley 22 and transecting it. The thumb may be flexed and extended multiple times to ensure a complete transection. When the A1 pulley 22 is transected, the slide 15 on the handle may be moved proximally along the handle to slide the cutting blade 12 back into the shaft 13 and to bring the anchoring tip 11 back toward the shaft 13. In this inactive configuration, the trigger thumb treatment device 10 may be removed from the thumb.

Figure 4:
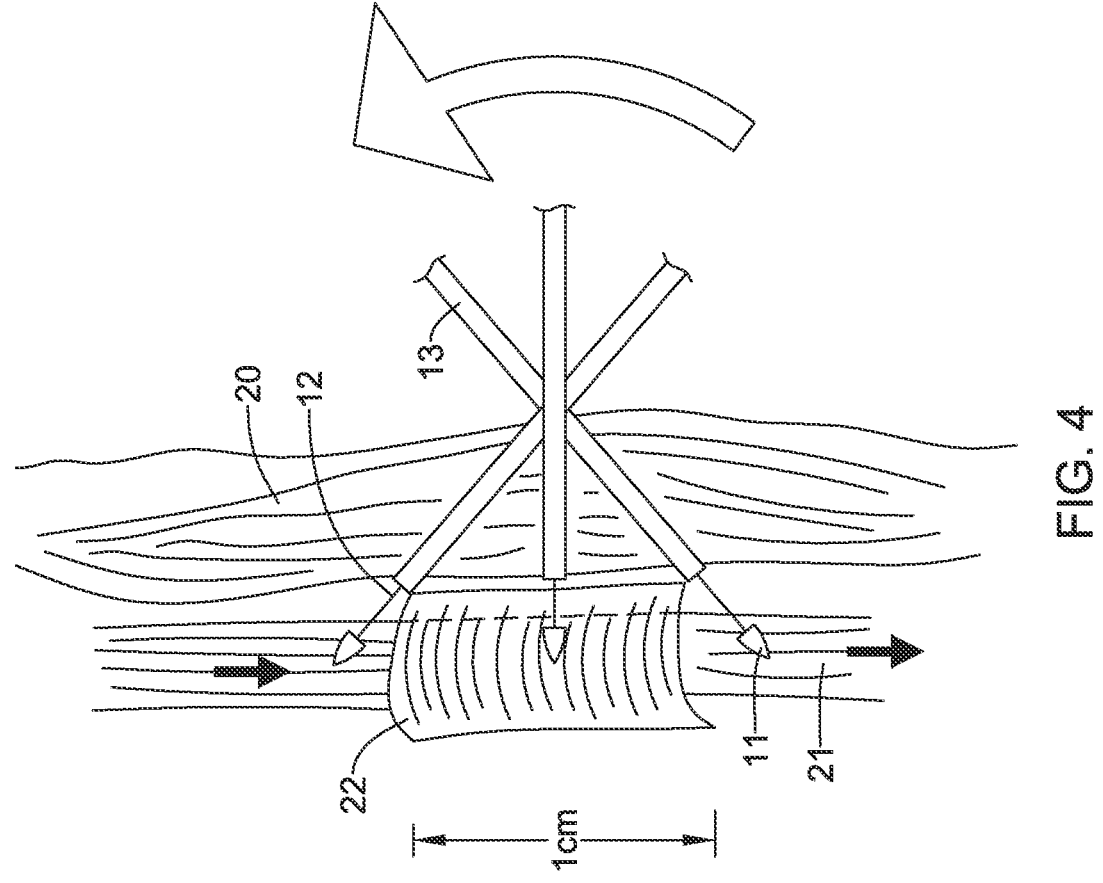
FIG. 4 is a top view, depicting a cross-sectional view of a portion of a thumb, illustrating a method of using the trigger thumb treatment device of FIGS. 1-2B to cut the A1 pulley of the thumb, according to one embodiment.

FIG. 4 is a different illustration of the method just described, from a top view and with a partial cross section of the thumb. In this illustration, the anchoring tip 11 starts at one end of the FPL tendon 21 (the top end in the drawing), and the shaft 13 of the treatment device is angled downward through the thenar muscle 20 and skin. As the thumb flexes, the FPL tendon 21 moves downward in the drawing, the anchoring tip 11 moves with it and the shaft 13 rotates about an axis at or near the skin. The blade 12 moves downward through the A1 pulley 22, thus transecting it.

Figures 5A, 5B:
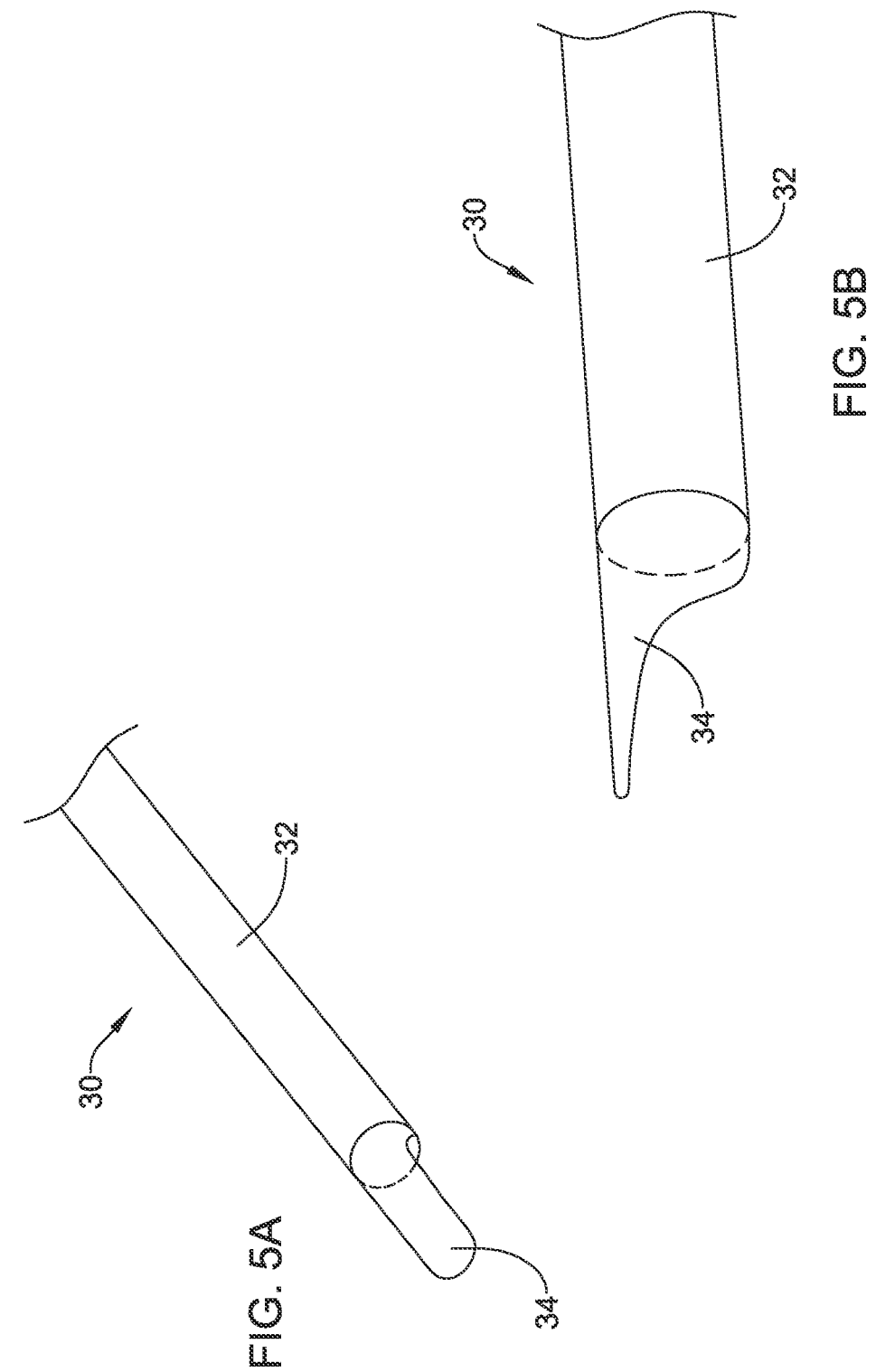
FIGS. 5A and 5B are top perspective and side views, respectively, of a conduit device for use in treating trigger thumb, according to one embodiment.

Referring now to FIGS. 5A and 5B, a conduit device 30 is illustrated, which may be used along with the trigger thumb treatment device 10. In alternative embodiments, the conduit device 30 may be used with other devices, such as trigger finger or carpal tunnel release devices. In this embodiment, the conduit device 30 includes a shaft 32 and a tip 34. The shaft 32 is made from a first material, and the tip 34 is made from a second material. (Alternatively, the shaft 32 and the tip 34 may be made from the same material.) The material for the tip 34 is selected so that ultrasound waves can pass through it and thus allow a user to visualize objects within or below the tip 34, such as the anchoring tip 11 and/or other portions of the trigger thumb treatment device 10. In other words, the tip 34 acts as an acoustic window that allows visualization of objects below it. The material of the shaft 32 is selected to have at least slightly different acoustic properties than the material of the tip 34. For example, the shaft material may be denser, have greater impedance, and/or the like, when compared to the tip material. The shaft 32 and the tip 34 may be attached to one another via any suitable means, such as but not limited to welding or gluing. The shaft 32 may be made of any suitable metal or polymer. Examples of materials for making the tip 34 include, but are not limited to, ABS, polystyrene, nylon, polycarbonate, PETG copolyester and glass-filled nylon.

In use, the conduit device 30 may be advanced through soft tissue to position the tip 34 at a desired treatment location. The trigger thumb treatment device 10 may then be advanced through the conduit device 30 and used to perform the procedure on the thumb. The tip 34 of the conduit device 30 allows for visualization of the distal end of the treatment device 10. In various embodiments, the conduit device 30 may be removed or left in place after initial placement of the treatment device 10.

Figure 6D:
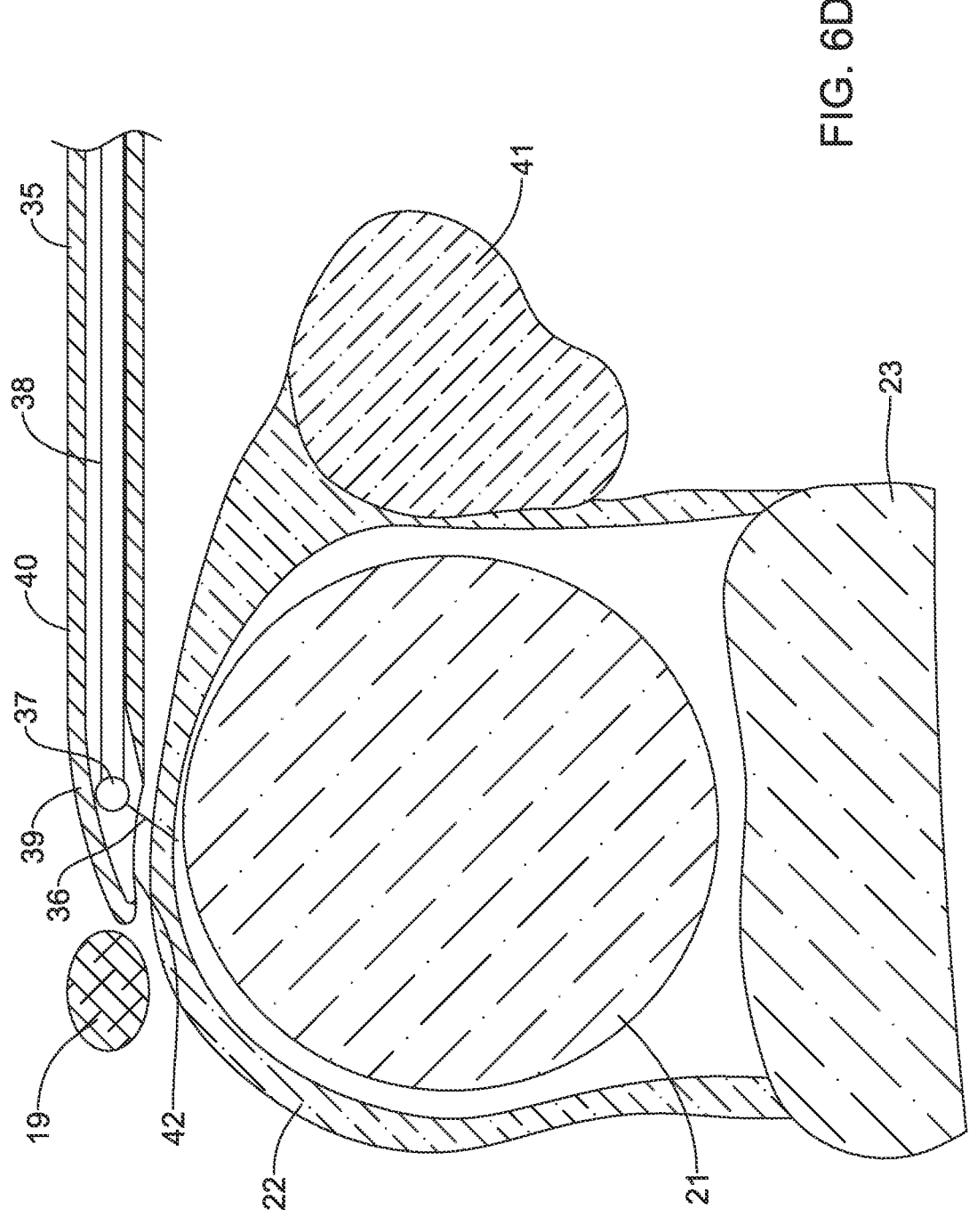
FIGS. 6D and 6E illustrate a method of using the treatment device of FIGS. 6A-6C.
Figure 6E:
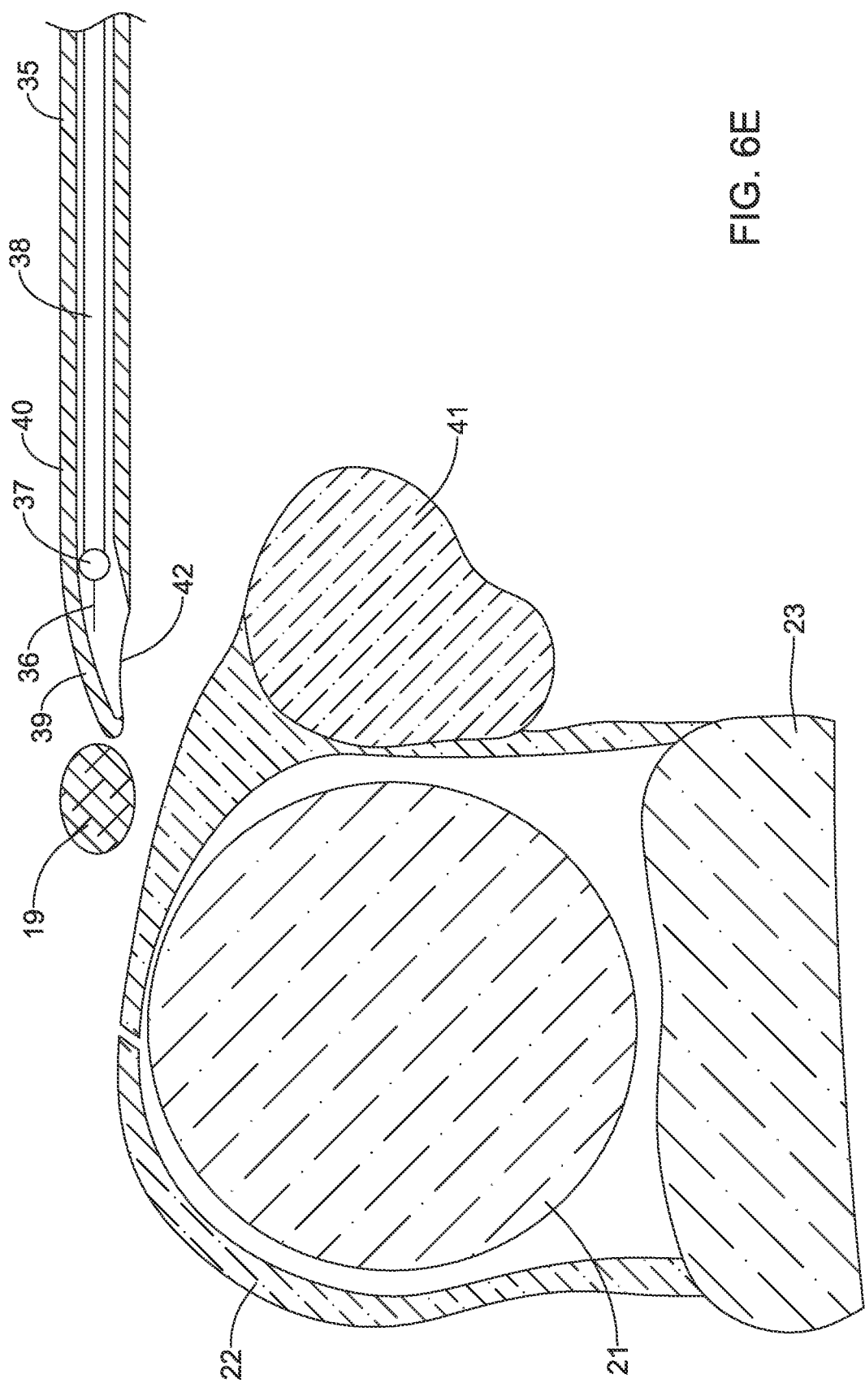

Referring now to FIGS. 6A-6E, one embodiment of a trigger thumb treatment device system 50 is illustrated, including a conduit device 35 (shown in cross-section in FIGS. 6C-6E) and a tissue treatment device 45 (shown from a side view in FIGS. 6A-6E). In some cases of trigger thumb, a sesamoid bone 41 may interfere with the transmuscular treatment approach described above. For such cases, the trigger thumb treatment system 50 illustrated in FIGS. 6A-6E is designed to safely approach and cut the A1 pulley 22 when a sesamoid bone 41 is present. The conduit device 35 includes a shaft 40 and a blunt tip 39, similar to (or the same as) the embodiment described above. The blunt tip 39 allows the conduit device 35 to be used to push or displace the proper digital nerve 19 in an ulnar direction, safely exposing the palmar surface of the A1 pulley 22 for transection. The tissue treatment device 45 includes a blade 36 attached via a hinge 37 a blade shaft 38. When the blade shaft 38 is advanced distally, the blade 36 becomes exposed (active) through an opening 42 on an inferior surface of the conduit device 35 (FIGS. 6C and 6D). In this active position, the blade 36 can be used to engage with and cut the palmar surface of the A1 pulley 22 (FIG. 6D). The blade 36 is oriented in a horizontal fashion (FIG. 6A and FIG. 6B), allowing the device to transect the A1 pulley in a distal to proximal direction or vice versa. FIG. 6E shows the conduit device 35 with the blade 36 of the tissue treatment device 45 not exposed (inactive) next to the palmar proper digital nerve 19 in its normal position. FIG. 6D shows the conduit device 35 with the tissue treatment device 45 in an active position (blade 36 exposed) over the FPL tendon 21 and the palmar aspect of the A1 pulley 22. In FIG. 6D, the conduit device 35 has been used to displace (move) the palmar proper digital nerve 19 in an ulnar direction, away from the exposed blade 36. After the A1 pulley 22 is transected, the tissue treatment device 45 may be inactivated and removed with the conduit, as in FIG. 6E.

Figures 7A, 7B:
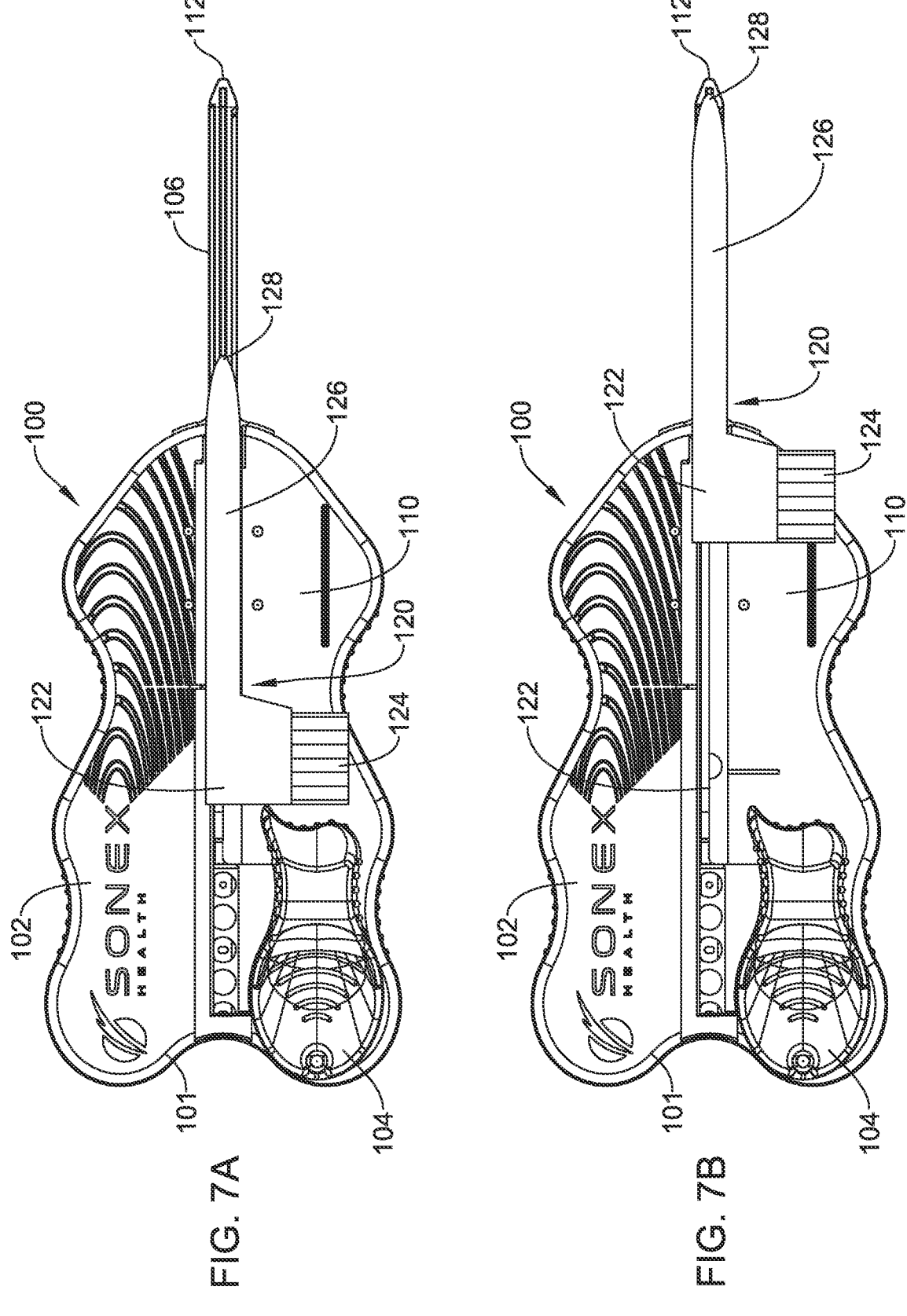
FIGS. 7A and 7B are top views of a trigger thumb treatment device, according to one embodiment.
Figure 7C:
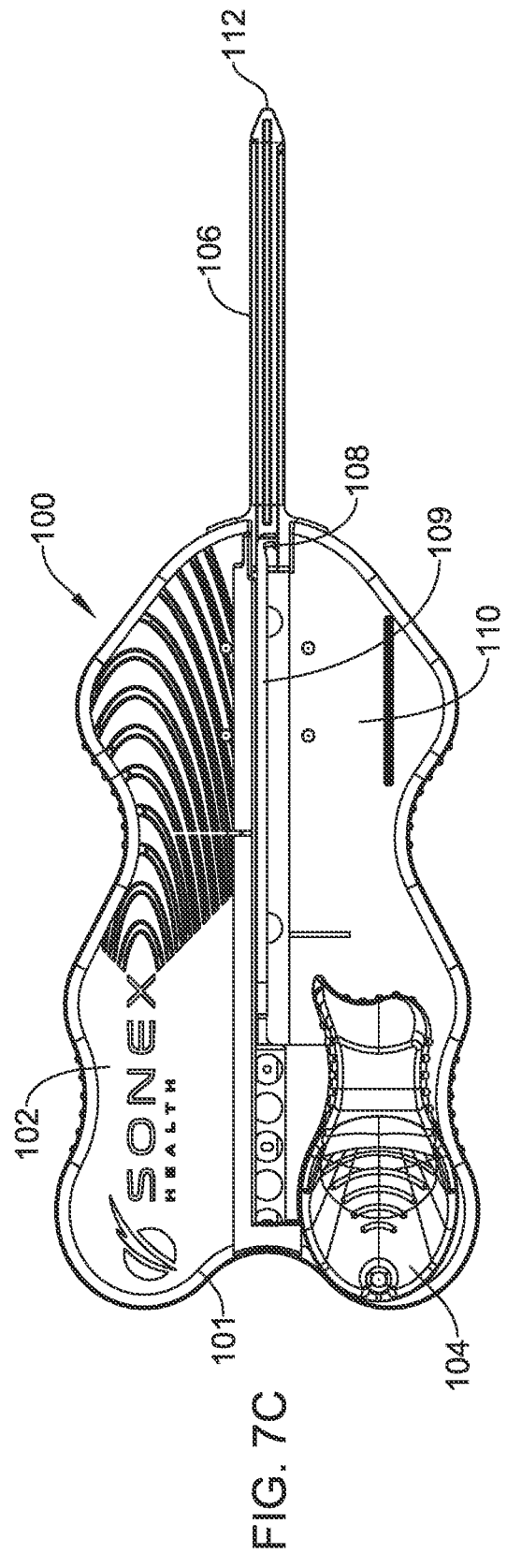
FIG. 7C is a top view of the trigger thumb treatment device of FIGS. 7A and 7B with a neurovascular guard removed.
Figure 7D:
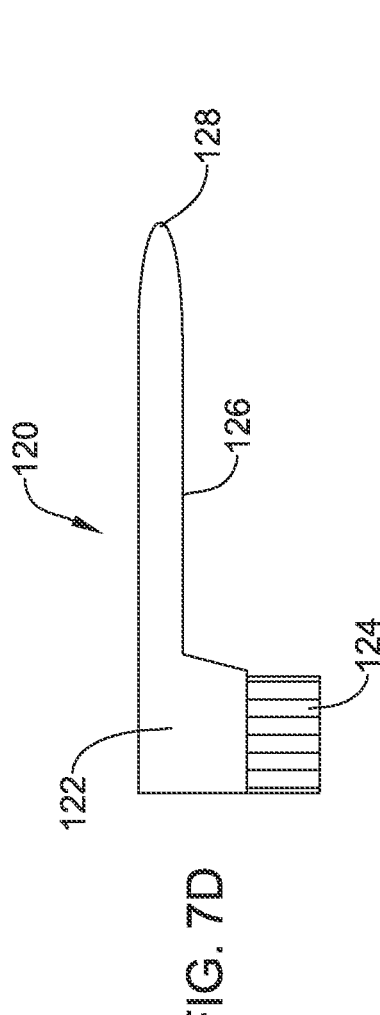
FIG. 7D is a top view of the neurovascular guard of the trigger thumb treatment device of FIGS. 7A and 7B.

Referring now to FIGS. 7A-7D, an alternative embodiment of a trigger thumb treatment device 100 is illustrated. The treatment device 100 includes a soft tissue cutting device 101 and a neurovascular guard 120. The soft tissue cutting device 101 is described in detail in U.S. patent application Ser. No. 17/733,532, entitled "CUTTING DEVICE FOR TRIGGER FINGER AND OTHER SOFT TISSUES," which was filed on Apr. 29, 2022, and which is hereby incorporated by reference in its entirety. In this embodiment, the soft tissue cutting device 101 includes a handle 102, a blade slider 104, an introducer shaft 106 with an introducer tip 112, a blade 108, a blade shaft 109, and a slot 110 on the handle 102 for accommodating a portion of the neurovascular guard 120. The neurovascular guard 120 includes a guard handle 122, a textured finger slide 124 for enhancing finger gripping ability, a shaft 126, and an atraumatic tip 128. When assembled, as in FIGS. 7A and 7B, the neurovascular guard 120 fits into the slot 110, for example via snap fit, so that it can slide along the slot 110. The neurovascular guard 120 can be moved from a retracted position (FIG. 7A) to an advanced or extended position (FIG. 7B). In the extended position, the atraumatic tip 128 of the neurovascular guard 120 is positioned near the introducer tip 112 but not all the way there, leaving a small gap between the two tips 128, 112. This allows the blade 108 to be advanced to the introducer tip 112 and exposed within the gap between the two tips 128, 112. The treatment device 100 may include a locking feature to lock the neurovascular guard 120 in the advanced position while performing a tissue cutting procedure.

The neurovascular guard 120 is designed to protect nerve tissue in the thumb from the blade 108 during a cutting procedure. As nerves in the thumb are typically closer to the area for cutting the A1 pulley than nerves in the other fingers are, the neurovascular guard 120 may be critically important for performing a safe trigger thumb release procedure with the device 100. In some embodiments, the neurovascular guard 120 is a monolithic structure made of a material that at least partially allows ultrasound waves to pass through it—in other words, the neurovascular guard 120 may be at least partially ultrasound lucent. To achieve this property, the neurovascular guard 120 may be made of any suitable material, such as any polymer with physical properties that allow adequate through-transmission or posterior enhancement, such as Ultem, PEEK, PPS, or the like. This specific polymer property will allow the user to create an ultrasound image deep to the neurovascular guard 120, making visible the introducer shaft 106 and the blade 108 during placement and transection of the A1 pulley.

Figure 8C:
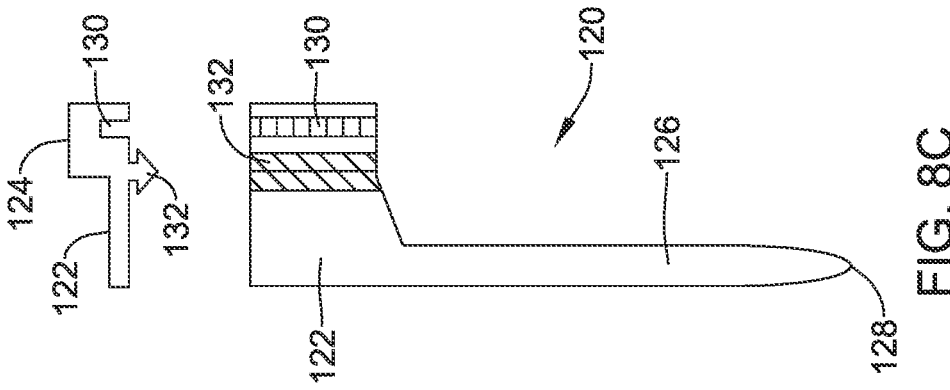
FIG. 8C is a bottom view (lower panel) and rear view (upper panel) of the neurovascular guard of FIG. 8A.
Figure 8B:
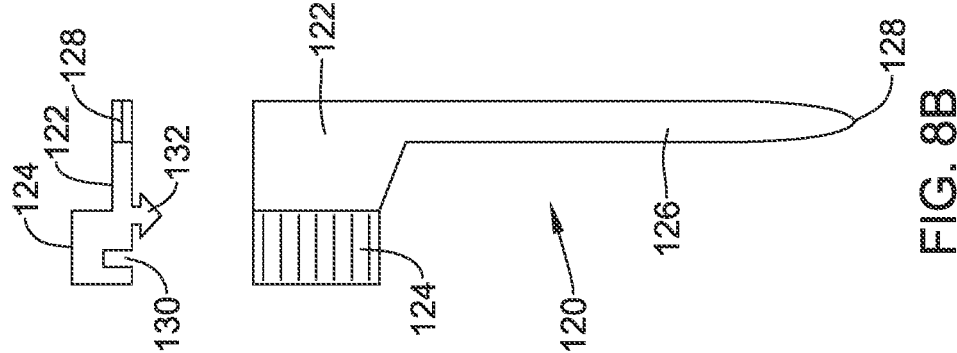
FIG. 8B is a top view (lower panel) and front view (upper panel) of the neurovascular guard of FIG. 8A.
Figure 8A:
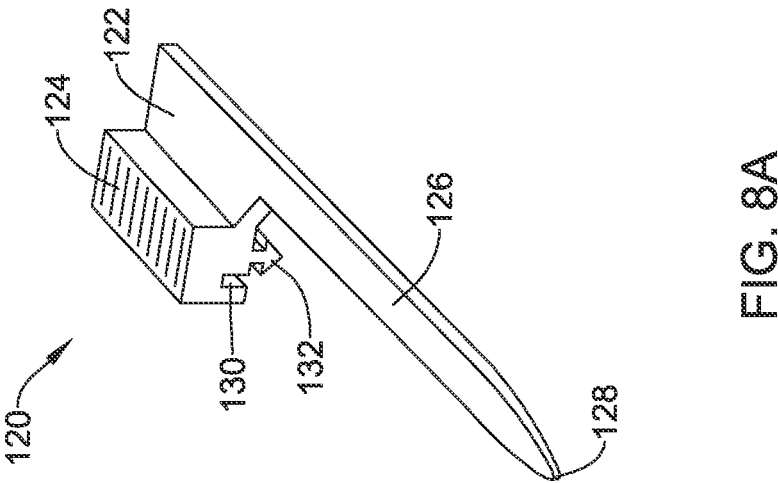
FIG. 8A is a top perspective view of the neurovascular guard of the trigger thumb treatment device of FIGS. 7A and 7B.

Referring now to FIGS. 8A-8C, the neurovascular guard 120 is illustrated in further detail. FIG. 8A is a perspective view, FIG. 8B is a top view (bottom panel) and front view (top panel), and FIG. 8C is a bottom view (bottom panel) and rear view (top panel). These figures show that the neurovascular guard 120 may include a guard slot 130 and a prong 132. The prong 132 is configured to snap-fit down into the slot 110 on the handle 102 of the device 100. The guard slot 130 is for receiving a longitudinal protrusion on the top surface of the handle 102, which is optional. These features are designed for connecting the neurovascular guard 120 to the handle 102 of the device 100 in a way that allows the neurovascular guard 120 to slide back and forth along the handle 102.

Figure 9A:
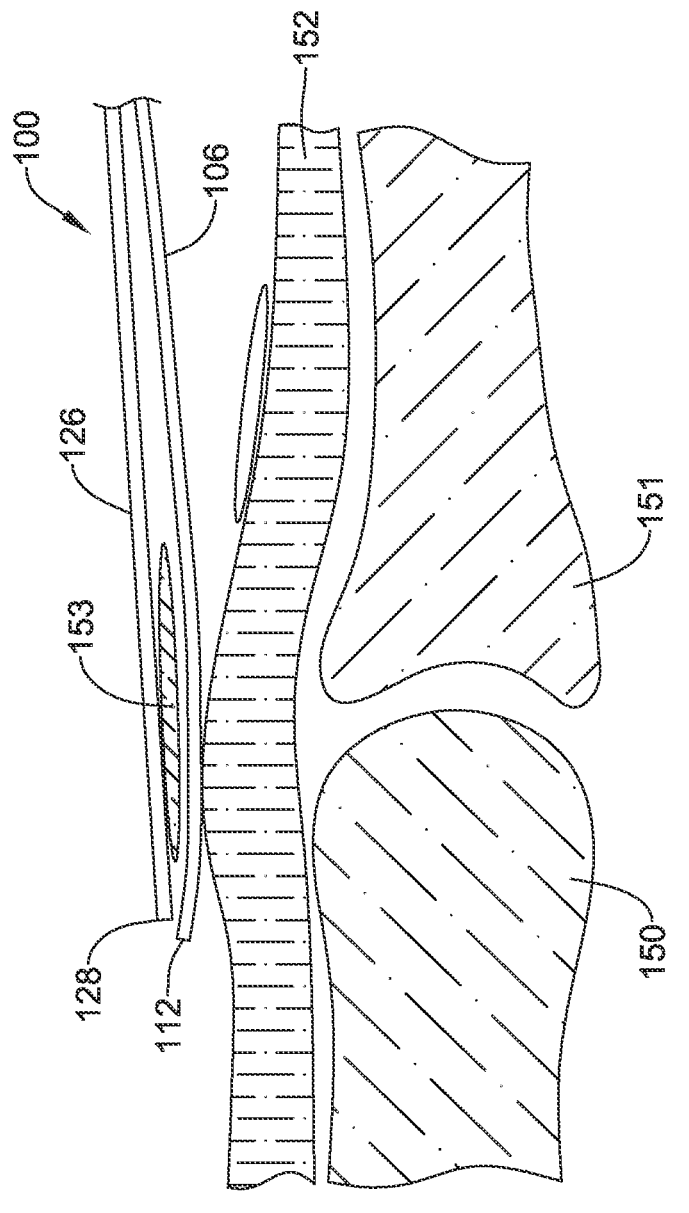
FIGS. 9A and 9B are lateral, cross-sectional views of a thumb and the trigger thumb treatment device, illustrating a method for treating trigger thumb, according to one embodiment.
Figure 9B:
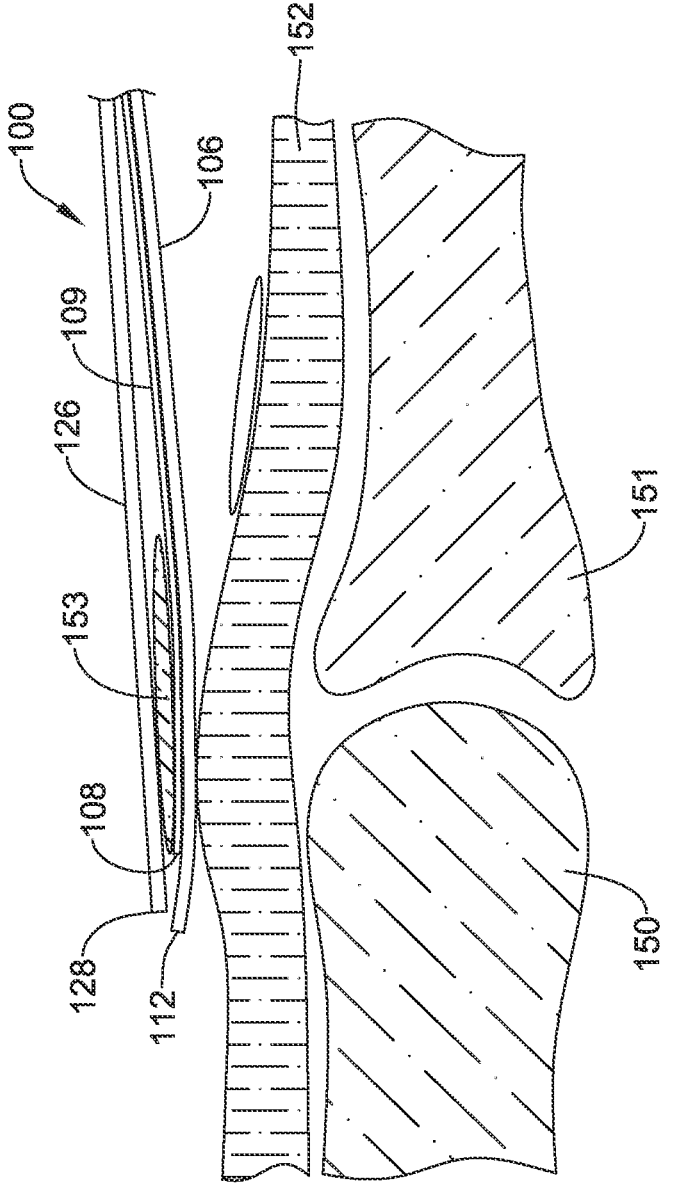
Figure 10:
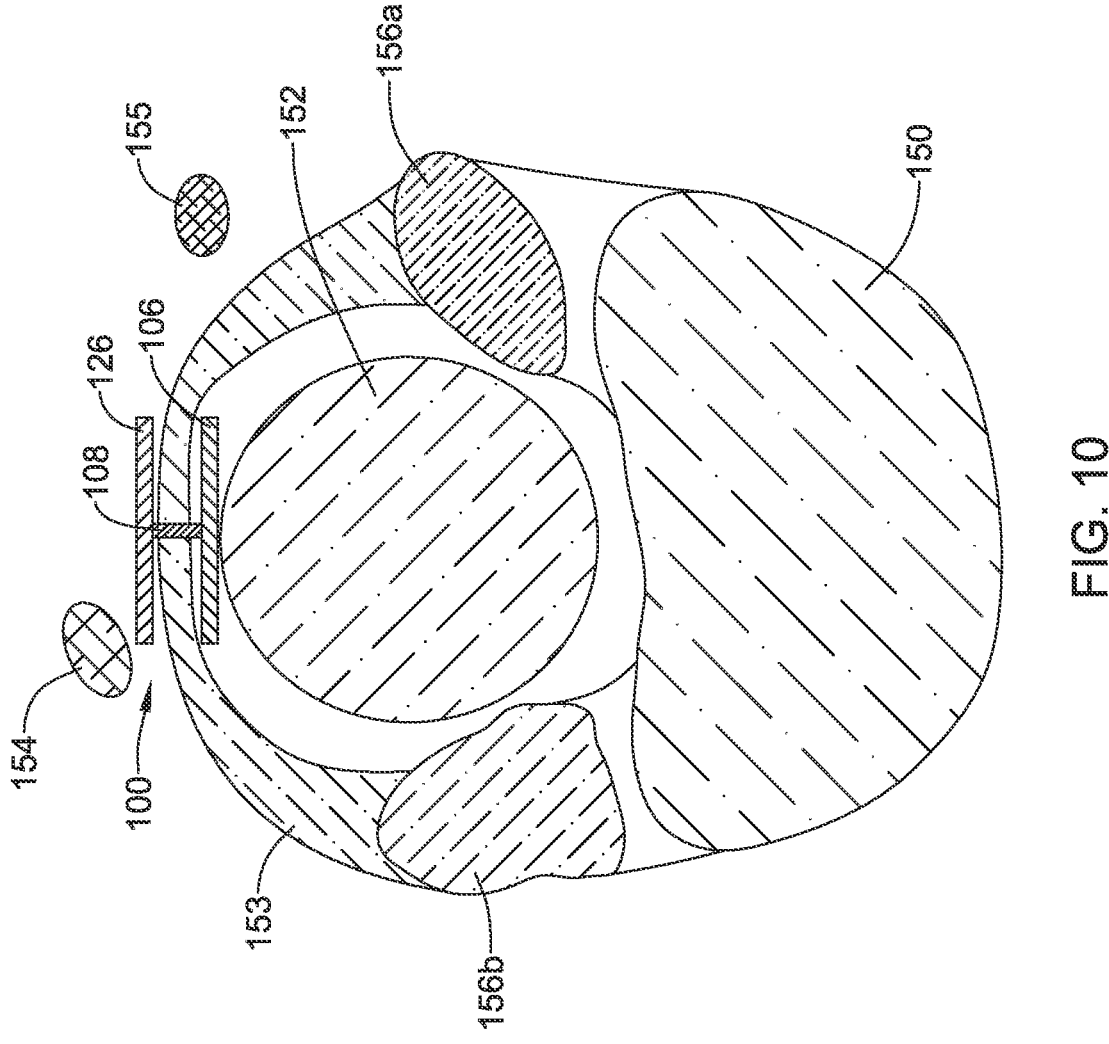
FIG. 10 is a frontal, cross-sectional view of a portion of a thumb, illustrating a method for treating trigger thumb, according to one embodiment.

Referring now to FIGS. 9A, 9B and 10, a method for performing a trigger thumb release procedure using the trigger thumb treatment device 100 (shown in a side view in FIGS. 9A and 9B) will be described. First, the anatomy shown in the figures will be described, with FIGS. 9A and 9B being lateral, cross-sectional views, and FIG. 10 being a frontal, cross-sectional view. The anatomical parts shown in FIGS. 9A and 9B are a first metacarpal bone 150, a first proximal phalanx 151, a flexor pollicis longus (FPL) tendon 152, and an A1 pulley 153. FIG. 10 also shows radial and ulnar digital nerve branches 154, 155 and two sesamoid bones 156a, 156b.

Referring to FIG. 9A, in one method embodiment, after surgical preparation in a sterile field and local anesthetic, the thumb is positioned in the slight extended position with the palm up. With ultrasound guidance, a small (e.g., 5 mm) horizontal incision is made approximately at the mid-point between the interphalangeal (IP) crease and the metacarpal phalangeal (MCP) crease, in a distal to proximal direction, down to the FPL tendon. Then, the introducer tip 112 is used to provide gentle blunt dissection of the region just superficial to the A1 pulley 153. Thereafter, the introducer tip 112 is advanced through the tendon sheath, superficial to the FPL tendon 152, and distally deep to the A1 pulley 153. The neurovascular guard 120 is unlocked and pushed via the finger slide 124 to the most distal position, so that the guard shaft 126 is superficial to the A1 pulley 153.

The slider 104 (or "blade handle") is then removed from the post and in the horizontal, inactive position, slid distally along the handle 102 to place the blade 108 deep to the A1 pulley 153, as depicted in FIG. 9B. The slider 104 is then rotated approximately 90 degrees (counterclockwise), placing the blade 108 in the active (vertical) position. The slider 104 is then pulled proximally, transecting the A1 pulley 153. The neurovascular guard 120 is then slid proximally. The introducer shaft 106 is then used to confirm complete A1 pulley transection and removed. If not confirmed, the above procedure is repeated by sliding the neurovascular guard 120 into place and repeating the cutting and confirmation procedure.

FIG. 10 shows the introducer shaft 106, the guard shaft 126, and the blade 108, in a position just before cutting the A1 pulley with the blade 108 in the active position. This view shows the proximity of nerves 154, 155 and thus the importance of the neurovascular guard 120.

Although the foregoing is believed to be a complete and accurate description of embodiments and features, the invention is not limited to any of the examples or embodiments described herein.

What is claimed is:
1. A method for treating a thumb of a patient, the method comprising:
    advancing an introducer shaft of a treatment device under
        an A1 pulley of the thumb, between the A1 pulley and a flexor pollicis longus (FPL) tendon of the thumb, wherein the introducer shaft is coupled with a handle of the treatment device;

sliding a guard handle along the handle of the treatment device to advance a neurovascular guard shaft of the treatment device along the shaft and over the A1 pulley, such that a gap remains between a distal tip of the neurovascular guard shaft and a distal tip of the introducer shaft;

rotating a blade slider approximately 90 degrees relative to the handle to expose a blade out of the gap between the distal tip of the introducer shaft and the distal tip of the neurovascular guard shaft and to position the blade in a vertical, cutting position;

retracting the blade by sliding the blade slider proximally along the handle to cut the A1 pulley; and removing the treatment device from the thumb.

2. The method of claim 1, further comprising visualizing at least part of the method using an ultrasound device positioned outside of the patient's hand.

3. The method of claim 2, wherein the neurovascular guard shaft is made of a material that allows the passage of ultrasound signals therethrough.

4. The method of claim 1, further comprising retracting the neurovascular guard shaft before removing the treatment device from the thumb.

\* \* \* \* \*